(12) United States Patent
Casper et al.

(10) Patent No.: US 8,946,198 B2
(45) Date of Patent: Feb. 3, 2015

(54) ESTROGEN REPLACEMENT REGIMEN

(76) Inventors: Robert Casper, Toronto (CA); Gideon Kopernik, Ramat-Hasharon (IL); Zeev Shoham, Ramat-Hasharon (IL)

(*) Notice: Subject to any disclaimer, the term of this patent is extended or adjusted under 35 U.S.C. 154(b) by 2671 days.

(21) Appl. No.: 10/526,064

(22) PCT Filed: Aug. 28, 2003

(86) PCT No.: PCT/CA03/01325
§ 371 (c)(1),
(2), (4) Date: Sep. 16, 2005

(87) PCT Pub. No.: WO2004/019954
PCT Pub. Date: Mar. 11, 2004

(65) Prior Publication Data
US 2006/0089337 A1 Apr. 27, 2006

Related U.S. Application Data

(60) Provisional application No. 60/406,331, filed on Aug. 28, 2002.

(51) Int. Cl.
*A01N 45/00* (2006.01)
*A61K 31/56* (2006.01)
*A61K 31/57* (2006.01)
*A61K 31/565* (2006.01)

(52) U.S. Cl.
CPC ............. *A61K 31/57* (2013.01); *A61K 31/56* (2013.01); *A61K 31/565* (2013.01)
USPC ............................................................ 514/170

(58) Field of Classification Search
USPC ............................................................ 514/170
See application file for complete search history.

(56) References Cited

U.S. PATENT DOCUMENTS

| | | | |
|---|---|---|---|
| 4,826,831 A * | 5/1989 | Plunkett et al. | 514/170 |
| 4,900,734 A * | 2/1990 | Maxson et al. | 514/171 |
| 4,957,119 A | 9/1990 | De Nijs | |
| 5,088,505 A | 2/1992 | De Nijs | |
| 5,108,995 A | 4/1992 | Casper | |
| 5,256,421 A | 10/1993 | Casper | |
| 5,276,022 A | 1/1994 | Casper | |
| 5,382,873 A | 1/1995 | Scholl et al. | |
| 5,422,119 A | 6/1995 | Casper | |
| 5,585,370 A | 12/1996 | Casper | |
| 6,653,298 B2 * | 11/2003 | Potter et al. | 514/182 |
| 2001/0027189 A1 * | 10/2001 | Bennink et al. | 514/171 |

OTHER PUBLICATIONS

Kurosawa et al. Endocrine Journal, Aug. 2002, vol. 49, No. 4, pp. 465-471.*
Bentel et al. Molecular & Cellular Endocrinology. 1999, vol. 154, pp. 11-20.*
Santell et al. 1997; J. Nutr. 127, pp. 263-269.*
Casper R F et al: "Estrogen and Interrupted Progestin: A New Concept for Menopausal Hormone Replacement Therapy" American Journal of Obstetrics & Gynecology, Mosby, St Louis, MO, US, vol. 168, No. 4, Apr. 1993 pp. 1188-1196, XP008000863.
"Estrogen Deprivation Causes Estradiol Hypersensitivity in Human Breast Cancer Cells" Shigeru Masamura et al. vol. 80, No. 10 Journal of Clinical Endocrinology and Metabolism; 2918-2925, 1995.
"Estrogen and interruped progestin: A new concept for menopausal hormone replacement therapy" Robert F. Casper, MD; 1188-1196, 1993.
"Short-Term Effects of Physiological and Pharmacological Does of Estradiol on Estrogen Receptor and Uterine Growth" Kevin L. Medlock et al. Journal of Receptor Research, 11(5), 743-756 (1991).
"Estradiol Down-Regulation of the Rat Uterine Estrogen Receptor" Kevin L. Medlock et al. 293-300, 1991.
"Stimulus summation and tachyphylaxis in estrogen response in sheep" W.H. Clewell 485-493, 1980.
"Regulation of the Estrogen Receptor and its Messenger Ribonucleic Acid in the Ovariectromized Sheep Myometrium and Endometrium: The Role of Estradiol and Progesterone" Wen Xuan Wu et al. Biology of Reproduction 55, 762-768 (1996).
"Preclinical evaluation of norgestimate, a progesitin with minimal androgenic activity" Audrey Phillips PhD et al. 1191-1196, 1992.
"Preformulation" Louis J Ravin, PhD, Chapter 76-Chapter 93, 1409-1677, 1985.

* cited by examiner

*Primary Examiner* — Samira Jean-Louis
(74) *Attorney, Agent, or Firm* — Norton Rose Fulbright Canada LLP

(57) ABSTRACT

The present invention provides an improved method to deliver estrogen to menopausal women comprising administering ultra-low dose estradiol alternating with standard-dose estradiol.

5 Claims, 4 Drawing Sheets

ESTROGEN REPLACEMENT REGIMEN

This application is a 371 of PCT/CA03/01325 filed on Aug. 28, 2003 which claims priority from provisional application 60/406,331 filed on Aug. 28, 2002.

FIELD OF THE INVENTION

The present invention relates to estrogen replacement for menopausal women and in particular providing estrogen replacement to menopausal women in such a way that cardiovascular response and other putative beneficial estrogen effects are maximized.

BACKGROUND OF THE INVENTION

Estrogen deficiency in the perimenopausal and menopausal woman is manifested by both short-term symptoms and long-term system illnesses. In the short term, the majority of women experience hot flushes and sweats associated with arousal from sleep. In addition, urogenital atrophy, decreased skin collagen and impaired balance may occur. Long-term, estrogen deficiency is associated with osteoporosis, heart disease, and possibly an increased risk of Alzheimer's disease in many women. Estrogen replacement therapy (ERT) is associated with clinical improvement in both short-term and long-term estrogen deficiency problems. Although there is a vast amount of data on the beneficial effects of estrogen on surrogate markers of potential cardiovascular benefit in molecular biology experiments and in animal and short-term human experiments, the clinical data related to long term prevention of disease is not always as expected. For example, a protective effect of estrogen on the cardiovascular system has been difficult to detect in prospective randomized trials. In addition, in some cases, hot flushes return despite the continuing use of long-term ERT. It is possible that estrogen treatment is physiologically appropriate, but the mode of estrogen administration might be problematic.

It is well known that progesterone or synthetic progestins downregulate progesterone receptors during continuous administration. Based on this observation, it was suggested that progesterone activity would be more efficient by "pulsed or intermittent administration" allowing both estrogen and progesterone receptors a chance for replenishment, as discussed in Casper, R. F. and Chapdelaine, A., Estrogen and interrupted progestin: a new concept for menopausal hormone replacement therapy, Am J Obstet Gynecol, 1993, April 168(4):1188-94; and in U.S. Pat. Nos. 5,108,995; 5,256,421; 5,276,022; 5,382,573; 5,422,119 and 5,585,370; and U.S. Application Ser. Nos. 60/369,629 and 60/369,707. All references are herein incorporated in their entirety.

In another approach discussed in Masamura et al., Estrogen deprivation causes estradiol hypersensitivity in human breast cancer cells, J Clin Endocrinol Metab 1995, October; 80(10):2918-25, it is postulated that enhanced sensitivity to estradiol (E2) may occur as a result of adaptation to low E2 levels after prolonged exposure to normal or supra-physiological levels of E2. Using a breast cancer cell line, they observed that breast cancer cells are able to adapt to low levels of estrogens by enhancing their sensitivity to E2.

In a study described in Wu et al., Regulation of the estrogen receptor and its messenger ribonucleic acid in the ovariectomized sheep myometrium and endometrium: the role of estradiol and progesterone, Biol Reprod 1996 October; 55(4):762-8, ovariectomized (OVX) non-pregnant sheep were used to analyze the role of estradiol and progesterone in the regulation of myometrial and endometrial estrogen receptor (ER) protein and ER mRNA in vivo. This group found that the effect of estradiol on ER expression is dose dependent. At supra-physiologic doses, estradiol inhibited ER expression, while physiologic concentrations of estradiol promoted ER expression.

In Clewell et al., Stimulus summation and tachyphylaxis in estrogen response in sheep, Am J Obstet Gynecol 1980 Nov. 1; 138 (5):485-93 (1980), it was shown that uterine blood flow is dependent on the initial estrogen concentration in the serum and the duration of the stimulus. It was concluded that prolonged, high-concentration exposure to estrogen results in tachyphylaxis.

In Medlock et al., Estradiol down-regulation of the rat uterine estrogen receptor, Proc Soc Exp Biol Med 1991 March; 196 (3):293-300, the effects of physiologic and pharmacologic doses of estradiol administered to adult ovariectomized rats via Silastic implants was examined. It was demonstrated that homologous down-regulation or loss of estrogen binding capacity was maximal at 24 hr and was completely reversible after implant removal. Of interest, the time required to recover from down-regulation was dose dependent. Medlock et al. concluded that estrogens can act as toxicants to the ER, especially when given chronically and in high doses. Subsequently, another study by Medlock et al. described in Medlock K L, et al., Short-term effects of physiological and pharmacological doses of estradiol on estrogen receptor and uterine growth, J Recept Res 1991; 11 (5):743-56, demonstrated that estradiol can down-regulate ER as early as 3 hours after exposure to pharmacologic doses and that the down-regulated state can be maintained by elevated E2 levels.

The present modes of delivering estrogen to postmenopausal women are oral, parenteral or transdermal. The oral administration exposes the body to a short daily peak of relatively high blood and hepatic estrogen levels, with rapid conversion to supra-physiological levels of less active estrone and inactive conjugated estrone sulphate. The parenteral and transdermal approaches deliver a steady level of estradiol with minimal hepatic metabolism. Epidemiological observations have to date not demonstrated major clinical differences between the various routes of estrogen administration. In current methods of administration, no time is given for ER replenishment by altering estrogen administration.

Prolonged administration of a constant dose of estradiol (either as continuous transdermal or daily oral bolus administration as given during HRT treatment) can decrease clinical response by down-regulation of estrogen receptors. This effect, as demonstrated in the present patent application, can be restored by intermittent administration of ultra-low doses of estrogen. It is reasonable to believe that by overcoming the possible estrogen receptor down-regulation effect observed with the conventional estrogen administration, the current proposed administration will result in better clinical response.

It is therefore desirable to provide an improved method to deliver estrogen to menopausal women and to overcome the limitations of the current methods.

SUMMARY OF THE INVENTION

In a broad aspect, the present invention provides an improved method to deliver estrogen to menopausal women comprising administering, either intermittently or pulsed, ultra-low dose estradiol alternating with standard-dose estradiol.

The present invention further provides an improved pharmaceutical preparation for administration to a female in need of estrogen replacement, comprising a plurality of doses arranged in alternating standard dose estrogen phases and ultra low dose estrogen phases, each phase consisting of from about 1 to about 4 consecutive daily unit doses or an equivalent thereof, wherein the daily unit doses of the standard dose estrogen phases each contain an amount of a substance exhibiting estrogenic activity equivalent to from at or about 0.5 mg to at or about 5.0 mg of estradiol, and the daily unit doses of the ultra-low dose estrogen phases contain an amount of a substance exhibiting estrogenic activity equivalent to at or about 0.005 mg to at or about 0.5 mg of estradiol.

The present invention further provides an improved pharmaceutical preparation, for administration to a female in need of estrogen and progesterone replacement therapy, comprising a plurality of doses arranged in alternating standard dose estrogen phases and ultra low dose estrogen phases, each phase consisting of from about 1 to about 4 consecutive daily unit doses or an equivalent thereof, wherein the daily unit doses of the standard dose estrogen phases each contain an amount of a substance exhibiting estrogenic activity equivalent to from at or about 0.5 mg to at or about 5.0 mg of estradiol and a substance exhibiting progestogenic activity equivalent to at or about 0 mg to at or about 300 mg of micronized progesterone and the daily unit doses of the ultra low dose estrogen phases contain a substance exhibiting estrogenic activity equivalent to from at or about 0.005 mg to at or about 0.5 mg and a substance exhibiting progestogenic activity equivalent to at or about 0 mg to at or about 300 mg of micronized progesterone.

The present invention further provides an improved pharmaceutical preparation for administration to a female in need of estrogen and progesterone replacement therapy comprising a plurality of doses arranged in alternating standard dose estrogen phases and ultra low dose estrogen phases, each phase consisting of from at or about 1 to at or about 4 consecutive daily unit doses or an equivalent thereof, wherein the daily unit doses of the standard dose estrogen phases each contain an amount of a substance exhibiting estrogenic activity, or an amount of a substance exhibiting estrogenic activity and an amount of a substance exhibiting progestogenic activity, and the daily unit doses of the ultra low dose estrogen phases each contain an amount of a substance exhibiting estrogenic activity and an amount of a substance exhibiting progestogenic activity, the amount of the substance exhibiting progestogenic activity being alternately increased in the ultra low dose estrogen phases to provide daily unit doses exhibiting progestin dominant activity and decreased in the standard dose estrogen phases to provide daily unit doses exhibiting lower progestin activity relative to the ultra low dose phases, and wherein the amount of substance exhibiting estrogenic activity per unit dose in the standard dose estrogen phase exhibits an estrogen activity equivalent to from at or about 0.5 mg to at or about 5.0 mg of estradiol, and the amount of substance exhibiting estrogenic activity per unit dose in the ultra low dose estrogen phase exhibits an estrogen activity equivalent to from at or about 0.0005 mg to at or about 0.5 mg of estradiol and the amount of substance exhibiting progestogenic activity per unit dose ranges from 0 to an amount which exhibits a progestin activity equivalent to at or about 300 mg of micronized progesterone.

The present invention further provides an improved pharmaceutical regimen for administration to a female in need of estrogen and progesterone replacement therapy comprising repeating cycles of a pharmaceutical regimen, each cycle having a series of from at or about twenty-eight to at or about thirty consecutive daily unit doses arranged in alternating standard dose estrogen phases and ultra low dose estrogen phases, each phase consisting of from about 1 to about 4 consecutive daily unit doses or an equivalent thereof, wherein the standard dose estrogen phases contain an amount of a substance exhibiting estrogen activity equivalent to from at or about 0.5 mg to at or about 5.0 mg of estradiol, and the daily unit doses of the ultra-low dose estrogen phases contain an amount of a substance exhibiting estrogenic activity equivalent to at or about 0.005 mg to at or about 0.5 mg of estradiol, wherein the daily unit doses administered from at or about day 16 to at or about day 30 further contain a substance exhibiting progestogenic activity equivalent to from 0 mg to at or about 300 mg of micronized progesterone.

In an alternative embodiment the present invention provides a package containing an improved pharmaceutical preparation for administration to a female in need of estrogen replacement, comprising a plurality of doses arranged in alternating standard dose estrogen phases and ultra low dose estrogen phases, each phase consisting of from about 1 to about 4 consecutive daily unit doses or an equivalent thereof, wherein the daily unit doses of the standard dose estrogen phases contain an amount of a substance exhibiting estrogenic activity equivalent to from at or about 0.5 mg to at or about 5.0 mg of estradiol, and the daily unit doses of the ultra-low dose estrogen phases contain an amount of a substance exhibiting estrogenic activity equivalent to at or about 0.005 mg to at or about 0.5 mg of estradiol.

In an alternative embodiment the present invention further provides a package containing an improved pharmaceutical preparation for administration to a female in need of estrogen and progesterone replacement comprising a plurality of doses arranged in alternating standard dose estrogen phases and ultra low dose estrogen phases, each phase consisting of from about 1 to about 4 consecutive daily unit doses or an equivalent thereof, wherein the daily unit doses of the standard dose estrogen phases contain an amount of a substance exhibiting estrogenic activity equivalent to from at or about 0.5 mg to at or about 5.0 mg of estradiol and a substance exhibiting progestogenic activity equivalent to from 0 mg to at or about 300 mg of micronized progesterone and the daily unit doses of the ultra low dose estrogen phases contain a substance exhibiting estrogenic activity equivalent to from at or about 0.005 mg to at or about 0.5 mg and a substance exhibiting progestogenic activity equivalent to from at or about 50 mg to at or about 300 mg of micronized progesterone.

In an alternative embodiment the present invention further provides a package containing an improved pharmaceutical preparation for administration to a female in need of estrogen and progesterone replacement comprising a plurality of doses arranged in alternating standard dose estrogen phases and ultra low dose estrogen phases, each phase consisting of from at or about 1 to at or about 4 consecutive daily unit doses or an equivalent thereof, wherein the daily unit doses of the standard dose estrogen phases contain an amount of a substance exhibiting estrogenic activity, or an amount of a substance exhibiting estrogenic activity and an amount of a substance exhibiting progestogenic activity, and the daily unit doses of the ultra low dose estrogen phases contain an amount of a substance exhibiting estrogenic activity and an amount of a substance exhibiting progestogenic activity, the amount of the substance exhibiting progestogenic activity being alternately increased in the ultra low dose estrogen phases to provide daily unit doses exhibiting progestin dominant activity and decreased in the standard dose estrogen phases to provide daily unit doses exhibiting lower progestin activity relative to the ultra low dose phases, and wherein the amount of substance exhibiting estrogenic activity per unit dose in the standard dose estrogen phase exhibits an estrogen activity equivalent to from at or about 0.5 mg to at or about 5.0 mg of estradiol, and the amount of substance exhibiting estrogenic activity per unit dose in the ultra low dose estrogen phase exhibits an estrogen activity equivalent to from at or about 0.0005 mg to at or about 0.5 mg of estradiol the amount of substance exhibiting progestogenic activity per unit dose ranges from 0 to an amount which exhibits a progestin activity equivalent to at or about 300 mg of micronized progesterone.

In an alternative embodiment the present invention further provides a package containing at least one cycle of an improved pharmaceutical preparation for administration to a female in need of estrogen and progesterone replacement repeating cycles of a pharmaceutical regimen, wherein each cycle comprises a series of from at or about twenty-eight to at or about thirty consecutive daily unit doses arranged in alternating standard dose estrogen phases and ultra low dose estrogen phases, each phase consisting of from about 1 to about 4 consecutive daily unit doses or an equivalent thereof, wherein the standard dose estrogen phases contain an amount of a substance exhibiting estrogen activity equivalent to from at or about 0.5 mg to at or about 5.0 mg of estradiol, and the daily unit doses of the ultra-low dose estrogen phases contain an amount of a substance exhibiting estrogenic activity equivalent to at or about 0.005 mg to at or about 0.5 mg of estradiol, wherein the daily unit doses administered from at or about day 16 to at or about day 30 further contain a substance exhibiting progestogenic activity equivalent to from 0 mg to at or about 300 mg of micronized progesterone.

In an alternative embodiment the present invention further provides an improved method for administering estrogen to a female in need of estrogen replacement, comprising administering to said female a pharmaceutical regimen comprising a plurality of doses arranged in alternating standard dose estrogen phases and ultra low dose estrogen phases, each phase consisting of from about 1 to about 4 consecutive daily unit doses or an equivalent thereof, wherein the daily unit doses of the standard dose estrogen phases contain an amount of a substance exhibiting estrogenic activity equivalent to from at or about 0.5 mg to at or about 5.0 mg of estradiol, and the daily unit doses of the ultra-low dose estrogen phases contain an amount of a substance exhibiting estrogenic activity equivalent to at or about 0.005 mg to at or about 0.5 mg of estradiol.

In an alternative embodiment the present invention further provides an improved method for administering estrogen to a female in need of estrogen and progesterone replacement comprising a plurality of doses arranged in alternating standard dose estrogen phases and ultra low dose estrogen phases, each phase consisting of from about 1 to about 4 consecutive daily unit doses or an equivalent thereof, wherein the daily unit doses of the standard dose estrogen phases contain an amount of a substance exhibiting estrogenic activity equivalent to from at or about 0.5 mg to at or about 5.0 mg of estradiol and a substance exhibiting progestogenic activity equivalent to from 0 mg to at or about 300 mg of micronized progesterone and the daily unit doses of the ultra low dose estrogen phases contain a substance exhibiting estrogenic activity equivalent to from at or about 0.005 mg to at or about 0.5 mg and a substance exhibiting progestogenic activity equivalent to from at or about 50 mg to at or about 300 mg of micronized progesterone.

In an alternative embodiment the present invention further provides an improved method for administering estrogen to a female in need of estrogen and progesterone replacement comprising a plurality of doses arranged in alternating standard dose estrogen phases and ultra low dose estrogen phases, each phase consisting of from at or about 1 to at or about 4 consecutive daily unit doses or an equivalent thereof, wherein the daily unit doses of the standard dose estrogen phases contain an amount of a substance exhibiting estrogenic activity, or an amount of a substance exhibiting estrogenic activity and an amount of a substance exhibiting progestogenic activity, and the daily unit doses of the ultra low dose estrogen phases contain an amount of a substance exhibiting estrogenic activity and an amount of a substance exhibiting progestogenic activity, the amount of the substance exhibiting progestogenic activity being alternately increased in the ultra low dose estrogen phases to provide daily unit doses exhibiting progestin dominant activity and decreased in the standard dose estrogen phases to provide daily unit doses exhibiting lower progestin activity relative to the ultra low dose phases, and wherein the amount of substance exhibiting estrogenic activity per unit dose in the standard dose estrogen phase exhibits an estrogen activity equivalent to from at or about 0.5 mg to at or about 5.0 mg of estradiol, and the amount of substance exhibiting estrogenic activity per unit dose in the ultra low dose estrogen phase exhibits an estrogen activity equivalent to from at or about 0.0005 mg to at or about 0.5 mg of estradiol the amount of substance exhibiting progestogenic activity per unit dose ranges from 0 to an amount which exhibits a progestin activity equivalent to at or about 300 mg of micronized progesterone.

In an alternative embodiment the present invention further provides an improved method for administering estrogen and progesterone to a female in need of estrogen and progesterone replacement comprising administering to said female repeating cycles of a pharmaceutical regimen, each cycle having a series of from at or about twenty-eight to at or about thirty consecutive daily unit doses arranged in alternating standard dose estrogen phases and ultra low dose estrogen phases, each phase consisting of from about 1 to about 4 consecutive daily unit doses or an equivalent thereof, wherein the standard dose estrogen phases contain an amount of a substance exhibiting estrogen activity equivalent to from at or about 0.5 mg to at or about 5.0 mg of estradiol, and the daily unit doses of the ultra-low dose estrogen phases contain an amount of a substance exhibiting estrogenic activity equivalent to at or about 0.005 mg to at or about 0.5 mg of estradiol, wherein the daily unit doses administered from at or about day 16 to at or about day 30 further contain a substance exhibiting progestogenic activity equivalent to from 0 mg to at or about 300 mg of micronized progesterone.

In an alternative embodiment the present invention further provides the use of a substance exhibiting estrogenic activity in the preparation of a medicament characterized in that the medicament is for estrogen replacement, for administration to a female in need of such therapy, the medicament comprising a plurality of doses arranged in alternating standard dose estrogen phases and ultra low dose estrogen phases, each phase consisting of from about 1 to about 4 consecutive daily unit doses or an equivalent thereof, wherein the daily unit doses of the standard dose estrogen phases contain an amount of a substance exhibiting estrogenic activity equivalent to from at or about 0.5 mg to at or about 5.0 mg of estradiol, and the daily unit doses of the ultra-low dose estrogen phases contain an amount of a substance exhibiting estrogenic activity equivalent to at or about 0.005 mg to at or about 0.5 mg of estradiol.

In an alternative embodiment the present invention further provides the use of a substance exhibiting estrogenic activity and a substance exhibiting progestogenic activity in the preparation of a medicament characterized in that the medicament is for estrogen and progesterone replacement, for administration to a female in need of such therapy, the medicament comprising a plurality of doses arranged in alternating standard dose estrogen phases and ultra low dose estrogen phases, each phase consisting of from about 1 to about 4 consecutive daily unit doses or an equivalent thereof, wherein the daily unit doses of the standard dose estrogen phases contain an amount of a substance exhibiting estrogenic activity equivalent to from at or about 0.5 mg to at or about 5.0 mg of estradiol and a substance exhibiting progestogenic activity equivalent to from 0 mg to at or about 300 mg of micronized progesterone and the daily unit doses of the ultra low dose estrogen phases contain a substance exhibiting estrogenic activity equivalent to from at or about 0.005 mg to at or about 0.5 mg and a substance exhibiting progestogenic activity equivalent to from at or about 50 mg to at or about 300 mg of micronized progesterone.

In an alternative embodiment the present invention further provides the use of a substance exhibiting estrogenic activity and a substance exhibiting progestogenic activity in the preparation of a medicament characterized in that the medicament is for estrogen and progesterone replacement, for administration to a female in need of such therapy, the medicament comprising a plurality of doses arranged in alternating standard dose estrogen phases and ultra low dose estrogen phases, each phase consisting of from at or about 1 to at or about 4 consecutive daily unit doses or an equivalent thereof, wherein the daily unit doses of the standard dose estrogen phases contain an amount of a substance exhibiting estrogenic activity, or an amount of a substance exhibiting estrogenic activity and an amount of a substance exhibiting progestogenic activity, and the daily unit doses of the ultra low dose estrogen phases contain an amount of a substance exhibiting estrogenic activity and an amount of a substance exhibiting progestogenic activity, the amount of the substance exhibiting progestogenic activity being alternately increased in the ultra low dose estrogen phases to provide daily unit doses exhibiting progestin dominant activity and decreased in the standard dose estrogen phases to provide daily unit doses exhibiting lower progestin activity relative to the ultra low dose phases, and wherein the amount of substance exhibiting estrogenic activity per unit dose in the standard dose estrogen phase exhibits an estrogen activity equivalent to from at or about 0.5 mg to at or about 5.0 mg of estradiol, and the amount of substance exhibiting estrogenic activity per unit dose in the ultra low dose estrogen phase exhibits an estrogen activity equivalent to from at or about 0.0005 mg to at or about 0.5 mg of estradiol the amount of substance exhibiting progestogenic activity per unit dose ranges from 0 to an amount which exhibits a progestin activity equivalent to at or about 300 mg of micronized progesterone In an alternative embodiment the present invention further provides the use of a substance exhibiting estrogenic activity and a substance exhibiting progestogenic activity in the preparation of a medicament characterized in that the medicament is for estrogen and progesterone replacement, for administration to a female in need of such therapy, the medicament comprising repeating cycles of a pharmaceutical regimen, each cycle having a series of from at or about twenty-eight to at or about thirty consecutive daily unit doses arranged in alternating standard dose estrogen phases and ultra low dose estrogen phases, each phase consisting of from about 1 to about 4 consecutive daily unit doses or an equivalent thereof, wherein the standard dose estrogen phases contain an amount of a substance exhibiting estrogen activity equivalent to from at or about 0.5 mg to at or about 5.0 mg of estradiol, and the daily unit doses of the ultra-low dose estrogen phases contain an amount of a substance exhibiting estrogenic activity equivalent to at or about 0.005 mg to at or about 0.5 mg of estradiol, wherein the daily unit doses administered from at or about day 16 to at or about day 30 further contain a substance exhibiting progestogenic activity equivalent to from 0 mg to at or about 300 mg of micronized progesterone.

All the embodiments described herein comprise embodiments wherein the daily unit doses are in at least one of orally, transdermally and buccally administerable form;

administering a series of consecutive daily doses arranged in standard dose estrogen phases of two daily unit doses each alternating with ultra low dose estrogen phases of two daily unit doses each;

administering a series of consecutive daily doses arranged in standard dose estrogen phases of three daily unit doses each alternating with ultra low dose estrogen phases of three daily unit doses each;

administering a series of consecutive daily doses arranged in standard dose estrogen phases of four daily unit doses each alternating with ultra low dose estrogen phases of four daily unit doses each, embodiments wherein the substance exhibiting progestin activity is selected on the basis that it binds to progestin receptors, demonstrates poor affinity for androgen receptors and has a lack of affinity for sex-hormone-binding globulin; and embodiments wherein the substance exhibiting estrogenic activity is selected from 17α-ethinylestradiol, esters and ethers of 17α-ethinylestradiol, 17α-ethinylestradiol 3-dimethylamino propionate, 17α-ethinylestradiol 3-cyclopentyl ether (quienestrol) and 17α-ethinylestradiol 3-methyl ether (mestranol); natural estrogens, estrone, estrone sulfate, estrone sulfate peperazine salt, estradiol and estriol, and their esters, conjugated equine estrogens and any components thereof with estrogenic activity, as well as the synthetic estrogens, and the substance exhibiting progestogenic activity is selected from desogestrel, norgestimate, gestodene, dydrogesterone, medroxyprogesterone acetate, norethynodrel, norethinedrone, norethinedrone acetate, levonorgestrel, dl-norgestrel, cyproterone acetate, chlormadinone acetate, magestrol acetate, 17 D-acetyl norgestimate, dienogest, trimegestone, drosperinone and nomagestrel.

BRIEF DESCRIPTION OF THE DRAWINGS

The invention will be better understood with reference to the attached description and the following figures, wherein.

DETAILED DESCRIPTION OF THE INVENTION

Figure 1:
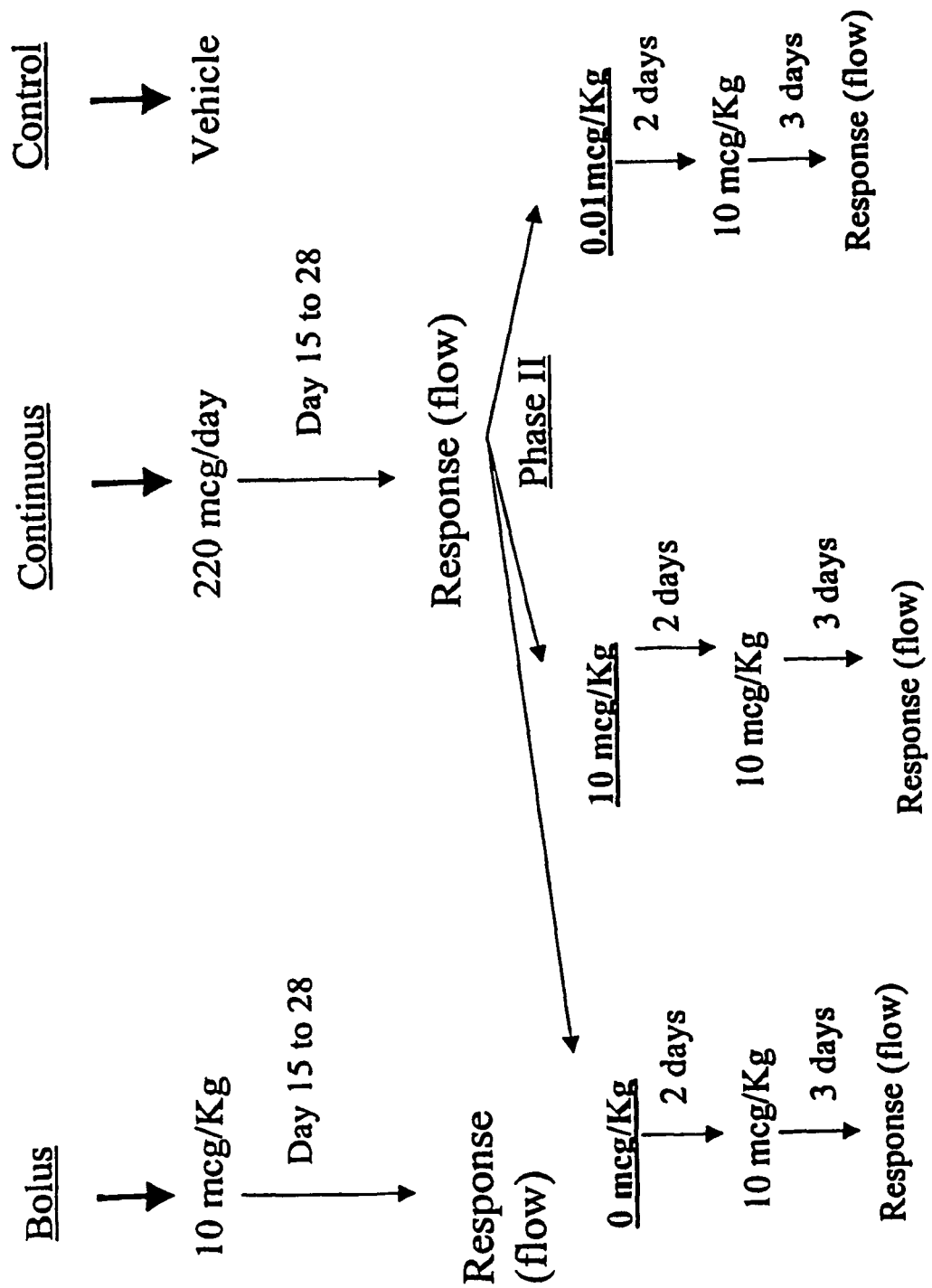
FIG. 1 is a graph that illustrates the experimental protocol of the second phase of a study, outlined in the description.

There is a current controversy as to whether ERT really provides cardioprotection to women based on inconclusive results of properly randomized and controlled clinical trials. It is possible that current estrogen replacement regimens involving oral conjugated equine estrogens (with a longer circulating and tissue half-time than natural estradiol) or transdermal continuous estradiol delivery may both result in decreased ER responses in the cardiovascular system over time. The use of the intermittent ultra-low dose estrogen replacement regimen of the present invention may be used to normalize ER vascular responses and restore the protective effects of estrogen replacement on the cardiovascular system.

As discussed above, current methods of administration of estrogen to postmenopausal women do not allow for ER replenishment by altering the estrogen administration. In order to address this issue, a study was conducted to answer the questions: Is there a difference in uterine blood flow response to intermittent vs. continuous exposure to estradiol? Does continuous exposure to estrogen in the dose used therapeutically down-regulate the uterine vascular response? Can ultra-low doses of estrogen given intermittently renew the response? The methodology and the results of the study are discussed below.

In the study, fifteen non-pregnant, oophorectomized ewes were implanted with doppler flow probes (Transonic System, Ithaca, N.Y.) on the uterine artery and indwelling catheters were placed in the femoral artery and vein for mean arterial pressure (MAP) measurements and estrogen administration respectively. All animals were oophorectomized. MAP, heart rate (HR) and uterine blood flow (UBF) were recorded for 30 minutes daily for 14 days after at least 60 minutes of adaptation in the recording room. A baseline for each parameter of each sheep was established by averaging values obtained from day 8 through 14 after the last surgery. On day 14, sheep were divided randomly into three groups consisting of 5 animals each. Group One (Continuous) received continuous infusion of 220 µg of 17β-estradiol daily into the femoral vein. The second group (Bolus) received a daily single bolus of 10 µg/kg of 17β-estradiol into the femoral vein. The third group (Control) served as a vehicle control. Treatment groups received estrogen from day 15 through 28 and parameters were recorded daily throughout this period.

In the second phase of the study an ultra-low dose of estrogen (0.01 µg/Kg) was administered to try to restore the response, which was most diminished in the first phase of the study by continuous infusion.

The bolus administration of estradiol (representative of daily oral ERT administration in women) produced a gradual increase in UBF in the first 4 days, and a daily reproducible plateau thereafter (from 489±206.5% to 1028-1448±380-489%). UBF returned almost to baseline levels after 24 hours (before the next bolus). The bolus administration did not affect MAP but produced a daily intermittent increase in HR (15-20%), which decreased to levels below the baseline after 24 hours (8-10%). The continuous administration (reflecting the situation with transdermal estrogen replacement in women) produced a significant increase in UBF by 1854.2±527.9% at two days of treatment, but thereafter UBF returned almost to baseline levels for the next 12 days of the study. During continuous estrogen administration, MAP decreased by 8.6±4% in the first two days and gradually increased to baseline levels during the rest of the study. HR increased significantly on the first day, dropped to baseline levels on the second day and gradually increased thereafter. It seems that none of the outcome parameters achieved a steady state during the study period. The control group did not demonstrate any significant changes in any parameter.

The second phase of the study involved continuous infusion of 220 µg of estradiol from day 15 to 28 in another 15 sheep followed by randomization into 3 groups (See FIG. 1). Group 1 (Control) received saline bolus infusion (0 µg 17β-estradiol/Kg) for 2 days followed by 3 daily bolus doses of 17β-estradiol (10 µg/Kg). The second group (Standard Bolus) received daily bolus doses of 17β-estradiol (10 µg/Kg) for 2 days followed by daily bolus doses of 17β-estradiol (10 µg/Kg) for another 3 days, The third group (Ultra-low E2 bolus) received daily bolus doses of 17β-estradiol (0.01 µg/Kg) for 2 days followed by standard daily bolus doses of 17β-estradiol (10 µg/Kg) for 3 days. UBF was measured throughout the study.

Figure 2:
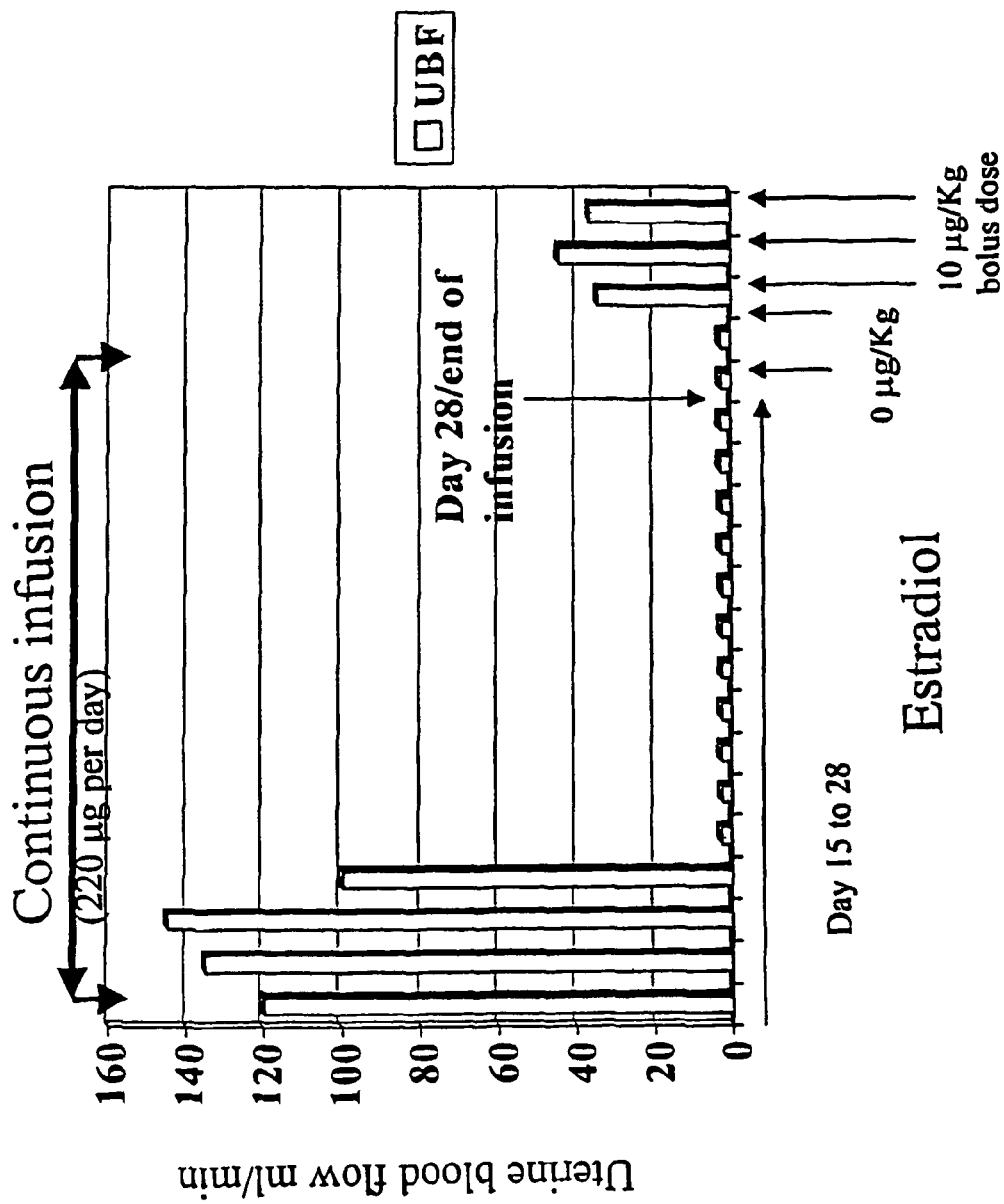
FIG. 2 is a graph that illustrates the results of the study outlined in FIG. 1 and the description, for the vehicle control group.
Figure 3:
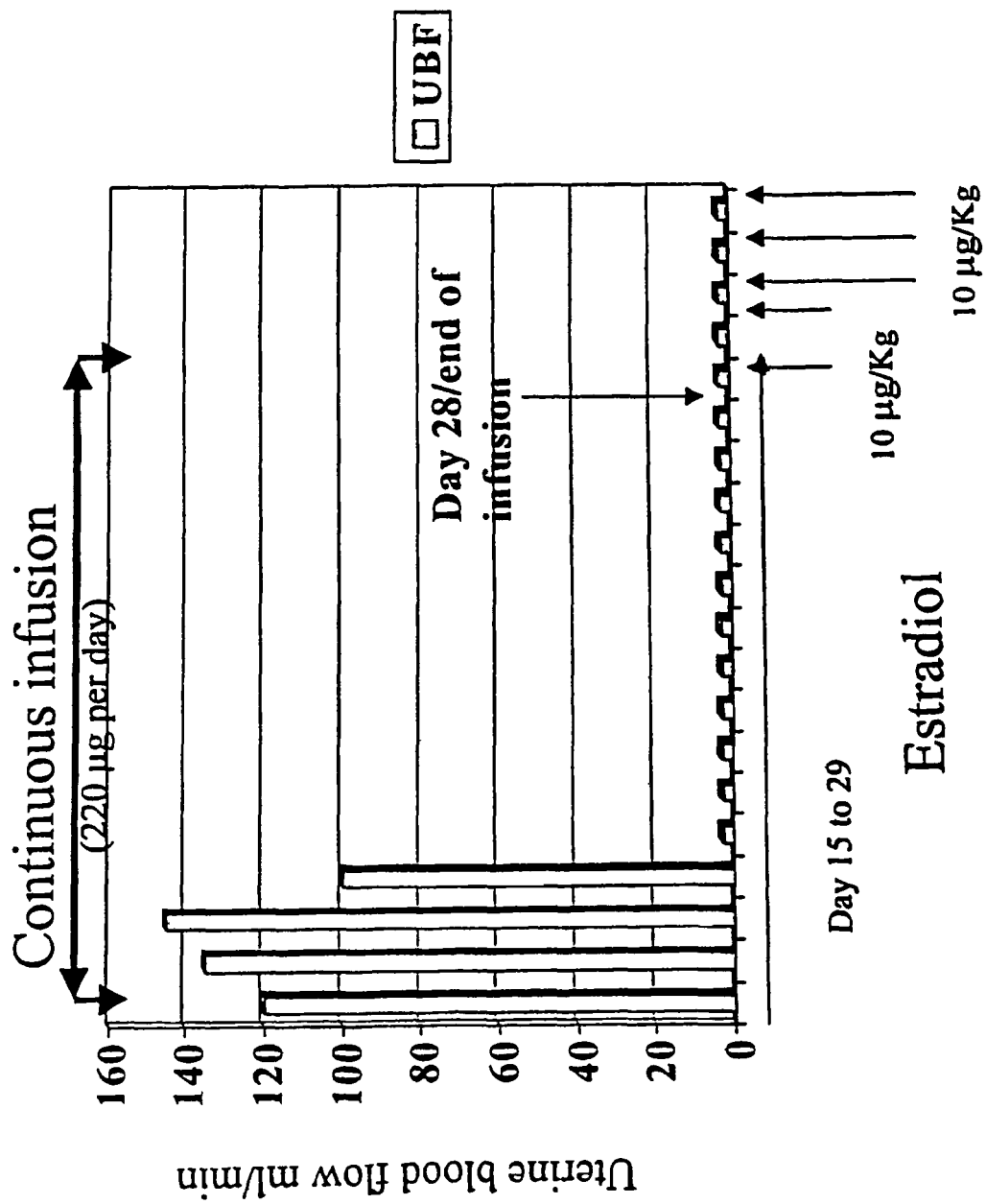
FIG. 3 is a graph that illustrates the results of the study outlined in FIG. 1 and the description, for the standard dose group.
Figure 4:
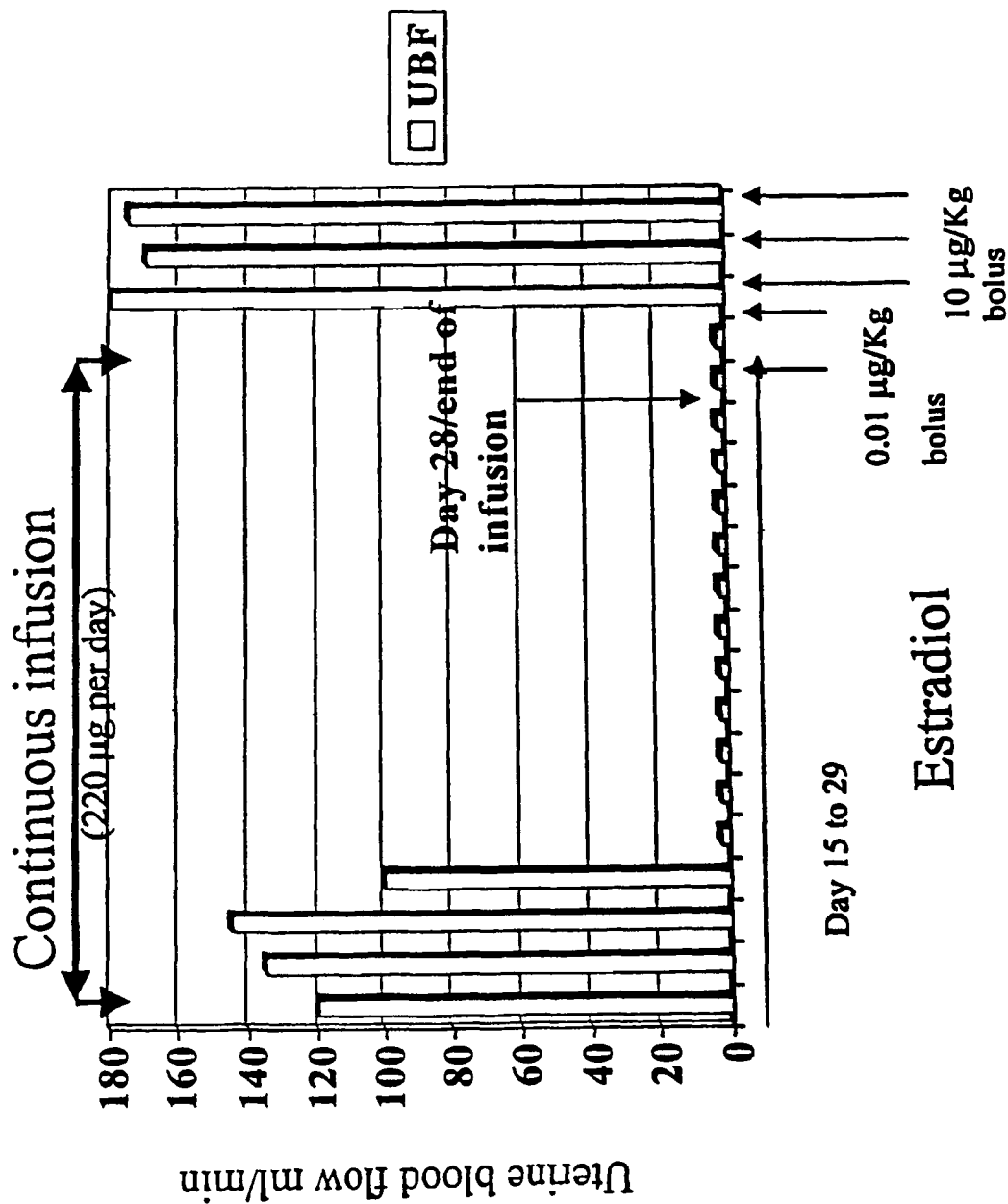
FIG. 4 is a graph that illustrates the results of the study outlined in FIG. 1 and the description, for the ultra low dose group.

Following the administration of the saline boluses for 2 days in the Control group, a partial response in UBF was observed with standard bolus 17β-estradiol doses (FIG. 2). Following the administration of the standard boluses of 17β-estradiol (10 µg/Kg) for 2 days in the Standard bolus group, no response at all was seen in UBF after 3 more days of 10 µg/Kg 17β-estradiol boluses. UBF remained completely suppressed (FIG. 3). In contrast, a complete response in UBF back to maximal levels was observed in the Ultra-low E2 bolus group, in which daily bolus doses of 17β-estradiol (0.01 µg/Kg) for 2 days were followed by standard daily bolus doses of 17β-estradiol (1 µg/Kg) for 3 days (FIG. 4).

The bolus administration of estrogen (similar to oral administration of estrogen clinically) produced a significant increase in uterine blood flow, which was reproducible. In contrast, the animals receiving the constant infusions of estrogen (similar to transdermal estrogen administration clinically) had a significant increase in uterine blood flow on days 15 and 16 but then flow returned to baseline and remained there for the rest of the study. It was possible to restore the vanishing response in UBF to maximal levels by intermittent ultra-low dose estrogen administration.

The present invention provides an intermittent or pulsed administration of ultra-low estrogen alternating with standard-dose estrogen as an improved method to deliver estrogen to postmenopausal women and to overcome the limitation of the current available methods concerning ER down-regulation. The present invention provides a more physiological approach and thus better response to treatment.

The preferred embodiment of the pharmacological preparation of the present invention comprises alternating doses of estrogen selected from standard available doses with ultra-low doses of estrogen as a pulsed estrogen replacement therapy.

DEFINITIONS

A Substance Exhibiting Estrogenic Activity

Any substance that exhibits appropriate estrogenic activity may be used in the present invention. As indicated the preferred estrogen is 17β-estradiol. Other suitable estrogens include, but are not limited to, estradiol valerate, other estrogens, 17α-ethinylestradiol, esters and ethers of 17α-ethinylestradiol such as, for example, 17α-ethinylestradiol 3-dimethylamino propionate, 17α-ethinylestradiol 3-cyclopentyl ether (quienestrol) and 17α-ethinylestradiol 3-methyl ether (mestranol). Natural estrogens such as estrone, estrone sulfate, estrone sulfate piperazine salt, estradiol and estriol, and their esters, conjugated equine estrogen and any components thereof with estrogenic activity, may also be employed. The selection of the estrogen and the dose level will generally follow from the literature, which is well known to the person skilled in the art.

A Substance Exhibiting Progestogenic Activity

The discussion that follows about the selection of a progestin and its dose level may be used as a guide in the selection of the physiologic replacement dose of estrogen, discussed above.

Progestins are classified, in agreement with their structures, in various groups which include progesterone, retroprogesterones, 17α-hydroxyprogesterones, 19-norprogesterones, 17α-hydroxyprogesterone derivatives, androstane and estrane derivatives.

The preferred progestin is micronized progesterone or a third generation progestin with similar affinity to the androgen receptor as natural progesterone, such as desogestrel or norgestimate. Desogestrel is also known under its chemical name 13-ethyl-11-methylene-18,19-dinor-17 alpha-pregn-4-en-20-yn-17-ol. While other progestins may be used in place of desogestrel or norgestimate, in selecting a suitable progestin, and in particular desogestrel or norgestimate, selection criteria include degree of affinity for the progesterone receptor, absence of affinity for the androgen receptor and whether the progestin displaced androgen from human sex-hormone-binding globulin (SHBG) [see Phillips, Audrey et al., Pre-clinical evaluation of norgestimate, a progestin with minimal androgenic activity, Am J Obstet Gynecology, October 1992, October 1992, Volume 167, Number 4, Part 2, pp. 1191-1196]. In the case of desogestrel and norgestimate, both bind to progesterone receptors, both demonstrate very poor affinity for androgen receptors and both have a lack of affinity for SHBG. All of these effects make these progestins similar to natural progesterone.

Other progestins may be employed in the present therapy regimen. Possible choices of those progestins include dydrogesterone, medroxyprogesterone acetate, norethynodrel, cyproterone acetate, chlormadinone acetate, magestrol acetate, 17 D-acetyl norgestimate, dienogest, trimegestone, drosperinone and nomagestrel, norethindrone, norethinedrone acetate, gestodene, levonorgestrel and d,l-norgestrel. The literature contains descriptions of numerous progestins and based on the criteria set out above, the person skilled in the art may make a suitable choice.

Examples of suitable daily doses of progestin include about 50 μg to about 200 μg of norgestimate and about 50 μg to about 200 μg of desogestrel. Equivalent doses for other progestins may be determined by the person skilled in the art by reference to the literature, for example the standard text *Treatment of the Menopausal Woman, Basic and Clinical Aspects*, Ed. Lobo, Rogerio A., Raven Press, New York, pp 73-80. Dosage selection is made with reference to hormone potency and the nature of the regimen. Other suitable doses can be based on an equivalent dose to the above two ranges. When making a choice of dose level, it would be a matter of routine experimentation for the person skilled in the art to take the equivalent dose level in the selected hormone and then to test a few doses around that level in order to refine the dose level.

Daily Doses or an Equivalent Thereof

The daily doses of the present invention may be administered in any convenient form. Preferred, as set out earlier is a single daily tablet, but any other suitable form may be employed. The single tablet is preferred as it reduces the likelihood that the patient will get confused. The words "an equivalent thereof" are meant to cover administrative forms that do not comprise daily doses, for example a transdermal form.

Generally speaking, the formulations are prepared according to conventionally known procedures in accordance with the desired method of administration. Different amounts of the active ingredients may be required in different types of formulations but it is essential that the amount of estrogenically active substance and progestationally active substance be selected so as to provide the dose equivalency for the regimen as described above. The percentage of active ingredients may vary according to the potency of the hormone, the delivery system or method of administration and is chosen in accordance with conventional methods known in the art.

The estrogen and progestogen compositions can be administered by way of any art recognized means as practiced in the pharmaceutical arts. For example, the estrogen and progestogen alone or in combination may be so formulated so that it can be administered orally, via a skin patch for transdermal absorption, by intramuscular injection, contained within an inert matrix which is implanted within the body and in a depot state, or intravaginally in a matrix that slowly releases the active compositions (such implants are taught for example in U.S. Pat. Nos. 4,957,119 and 5,088,505).

Pharmaceutical Preparations

The pharmaceutical compositions that can be prepared according to the invention are compositions for enteral, such as peroral or rectal administration, also for transdermal or sublingual administration, and for parenteral, for example intravenous, subcutaneous and intramuscular, administration. Suitable unit dose forms, especially for peroral and/or sublingual administration, for example dragees, tablets or capsules, comprise preferably from approximately 0.01 mg to approximately 20 mg, especially from approximately 0.1 mg to approximately 10 mg, of the combination of the above-mentioned compounds or of a pharmaceutically acceptable salt thereof, together with pharmaceutically acceptable carriers. The preferred form of administration is oral. The proportion of active ingredient in such pharmaceutical compositions is generally from approximately 0.001% to approximately 60%, preferably from approximately 0.1% to approximately 20%.

Suitable excipients for pharmaceutical compositions for oral administration are especially fillers, such as sugars, for example lactose, saccharose, mannitol or sorbitol, cellulose preparations and/or calcium phosphates, for example tricalcium phosphate or calcium hydrogen phosphate, and binders, such as starches, for example corn, wheat, rice or potato starch, gelatin, tragacanth, methylcellulose and/or hydroxypropylcellulose, disintegrators, such as the above-mentioned starches, also carboxymethyl starch, cross-linked polyvinylpyrrolidone, agar, alginic acid or a salt thereof, such as sodium alginate, and/or cellulose, for example in the form of crystals, especially in the form of microcrystals, and/or flow regulators and lubricants, for example silicic acid, talc, stearic acid or salts thereof, such as magnesium or calcium stearate, cellulose and/or polyethylene glycol.

Dragee cores can be provided with suitable, optionally enteric, coatings, there being used inter alia concentrated sugar solutions which may comprise gum arabic, talc, polyvinylpyrrolidone, polyethylene glycol and/or titanium dioxide, or coating solutions in suitable solvents or solvent mixtures, or, for the preparation of enteric coatings, solutions of suitable cellulose preparations, such as acetylcellulose phthalate or hydroxypropylmethylcellulose phthalate.

Other orally administrable pharmaceutical compositions are dry-filled capsules consisting of gelatin, and also soft sealed capsules consisting of gelatin and a plasticiser, such as glycerol or sorbitol. The dry-filled capsules may contain the active ingredient in the form of granules, for example in admixture with fillers, such as lactose, binders, such as starches, and/or glidants, such as talc or magnesium stearate, and, if desired, stabilisers. In soft capsules, the active ingredient is preferably dissolved or suspended in suitable oily excipients, such as fatty oils, paraffin oil or liquid polyethylene glycols, to which stabilisers and/or anti-bacterial agents may also be added. There may also be used capsules that are easily bitten through, in order to achieve by means of the sublingual ingestion of the active ingredient that takes place as rapid an action as possible.

Suitable rectally or transvaginally administrable pharmaceutical compositions are, for example, suppositories that consist of a combination of the active ingredient with a suppository base. Suitable suppository bases are, for example, natural or synthetic triglycerides, paraffin hydrocarbons, polyethylene glycols or higher alkanols. There may also be used gelatin rectal capsules, which contain a combination of the active ingredient with a base material. Suitable base materials are, for example, liquid triglycerides, polyethylene glycols or paraffin hydrocarbons.

Suitable formulations for transdermal administration comprise the active ingredient together with a carrier. Advantageous carriers include absorbable pharmacologically acceptable solvents that serve to facilitate the passage through the skin of the host. Transdermal systems are usually in the form of a bandage that comprises a support, a supply container containing the active ingredient, if necessary together with carriers, optionally a separating device that releases the active ingredient onto the skin of the host at a controlled and established rate over a relatively long period of time, and means for securing the system to the skin.

Suitable for parenteral administration are especially aqueous solutions of an active ingredient in water-soluble form, for example in the form of a water-soluble salt, and also suspensions of active ingredient, such as corresponding oily injection suspensions, there being used suitable lipophilic solvents or vehicles, such as fatty oils, for example sesame oil, or synthetic fatty acid esters, for example ethyl oleate, or triglycerides, or aqueous injection suspensions that comprise viscosity-increasing substances, for example sodium carboxymethylcellulose, sorbitol and/or dextran, and, optionally, stabilisers.

Dyes or pigments may be added to the pharmaceutical compositions, especially to the tablets or dragee coatings, for example for identification purposes or to indicate different doses of active ingredient.

Pharmaceutical compositions containing compounds of the invention may further comprise pharmaceutically acceptable carriers and be in either solid or liquid form. Solid preparations include powders, tablets, dispersible granules, capsules, etc. The carrier may also be one or more substances, which act as diluents, flavoring agents, solubilizers, lubricants, suspending agents, binders, or tablet disintegrating agents as well as encapsulating materials. Suitable carriers include magnesium carbonate, magnesium stearate, talc, lactose, sugar, peptin, dextrin, starch, methylcellulose, sodium carboxylmethylcellulose, and the like. Liquid form preparations include solutions, which are suitable for oral or parenteral administration, or suspensions and emulsions suitable for oral administration.

Sterile water solutions of the active component or sterile solutions of the active components in solvents comprising water, ethanol, or propylene glycol are examples of liquid preparations suitable for parenteral administration. Aqueous solutions for oral administration can be prepared by dissolving the active compound in water and adding suitable flavorants, coloring agents, stabilizers and thickening agents as required. Aqueous suspensions for oral use can be made by dispersing the active component in water together with a viscous material such as a natural or synthetic gum, methylcellulose, sodium carboxymethyl-cellulose, and other suspending agents known to the pharmaceutical formulation art. Other solid dosage forms include topical dosage forms which include solutions, powders, fluid emulsions, fluid suspensions, semi-solids, ointments, pastes, creams, gels or jellies and foams; and parenteral dosage forms which include solutions, suspensions, emulsions or dry powder comprising an effective amount of estrogen or estrogen and progestogen as taught in this invention.

Various conventional techniques for preparing pharmaceutical compositions including solutions, suspensions, tablets or caplets can be employed, as would be known to those skilled in the art and as is disclosed for example by Remington's Pharmaceutical Sciences, Mack Publishing Co., Part 8, Chapters 76-93, Pharmaceutical Preparations and Their Manufacture, pp. 1409-1677 (1985).

The pharmaceutical formulations may be provided in kit form containing preferably multiples of four unit dosages, each constituting an ultra low dose estrogenic phase and in a suitable form, for example, caplets or tablets. The kit may comprise a dial package or a foil strip as is well known in the art. The kit would typically contain an even number of doses for each phase arranged in an even number of ultra low dose estrogenic phases. Thus the unit dosages would be arranged in each package in multiples of eight so that an even number of phases would be present in each package.

The term "unit dosage form" as used herein refers to physically discrete units suitable as unit dosages, each unit containing a predetermined quantity of active ingredient calculated to produce the desired therapeutic effect in association with the required pharmaceutical carrier. The term "doses" as used herein broadly encompasses the term unit dosage form or dosage units as well as continuous dosing of compositions by depot or other methods.

The pharmaceutical compositions of the present invention can be prepared in a manner known per se, for example by means of conventional mixing, granulating, confectioning, dissolving or lyophilising processes. For example, pharmaceutical compositions for oral administration can be obtained by combining the active ingredient with solid carriers, optionally granulating a resulting mixture, and processing the mixture or granules, if desired or necessary after the addition of suitable excipients, to form tablets or dragee cores.

Standard-Dose Estrogen Phase

Examples of standard doses of estrogen that are administered in the standard dose estrogen phase are illustrated in the examples and in, for example, U.S. Pat. Nos. 5,422,119; 5,382,573; 5,256,421 and 5,108,995. Preferably, the standard dose of estrogen is sufficient to promote the development of progestin receptors in the endometrium of a female.

Ultra-Low Dose Estrogen Phase

Examples of ultra-low doses of estrogen that are administered in the ultra-low dose estrogen phases are illustrated in the examples provided. Preferably the ultra-low doses are at least one tenth of the standard dose that they are administered with in alternating phases.

Examples of suitable pharmaceutical preparations that can be made according to the invention are provided. It will be understood that the present invention is not limited to the examples provided.

EXAMPLE 1

Three-day phases of a daily unit dose in the form of a tablet of 0.625 mg of conjugated equine estrogen (CEE) and the following inactive ingredients: croscarmellose sodium, microcrystalline cellulose, magnesium stearate, ferric oxide red and lactose monohydrate and alternating with three-day phases of a daily unit dose in the form of a tablet of 0.0625 mg of CEE and the following inactive ingredients: croscarmellose sodium, microcrystalline cellulose, magnesium stearate, ferric oxide red and lactose monohydrate.

EXAMPLE 2

Three-day phases of a daily unit dose in the form of a tablet of 0.625 mg of conjugated equine estrogen (CEE) and the following inactive ingredients: croscarmellose sodium, microcrystalline cellulose, magnesium stearate, ferric oxide red and lactose monohydrate and alternating with three-day phases of a daily unit dose in the form of a tablet of 0.006 mg of CEE and the following inactive ingredients: croscarmellose sodium, microcrystalline cellulose, magnesium stearate, ferric oxide red and lactose monohydrate.

EXAMPLE 3

Three-day phases of a daily unit dose in the form of a tablet of 1 mg micronized estradiol and the following inactive ingredients: croscarmellose sodium, microcrystalline cellulose, magnesium stearate, ferric oxide red and lactose monohydrate and alternating with three-day phases of a daily unit dose in the form of a tablet of 0.01 mg micronized estradiol and the following inactive ingredients: croscarmellose sodium, microcrystalline cellulose, magnesium stearate, ferric oxide red and lactose monohydrate.

EXAMPLE 4

Three-day phases of a daily unit dose in the form of a tablet of 1 mg micronized estradiol and the following inactive ingredients: croscarmellose sodium, microcrystalline cellulose, magnesium stearate, ferric oxide red and lactose monohydrate and alternating with three-day phases of a daily unit dose in the form of a tablet of 0.001 mg micronized estradiol and the following inactive ingredients: croscarmellose sodium, microcrystalline cellulose, magnesium stearate, ferric oxide red and lactose monohydrate.

EXAMPLE 5

Three and a half-day phases of a daily unit dose in the form of a patch containing 50 μg per day transdermal estradiol and alternating with three and a half-day phases of a patch containing 0.5 μg per day transdermal estradiol.

EXAMPLE 6

Two-day phases of a daily unit dose in the form of a tablet of 1 mg micronized estradiol and the following inactive ingredients: croscarmellose sodium, microcrystalline cellulose, magnesium stearate, ferric oxide red and lactose monohydrate and alternating with two-day phases of a daily unit dose in the form of a tablet of 0.001 mg micronized estradiol and the following inactive ingredients: croscarmellose sodium, microcrystalline cellulose, magnesium stearate, ferric oxide red and lactose monohydrate.

These treatment examples will be used alone in women without a uterus or in women in whom a progestin-containing intrauterine device has been inserted. The present invention will be combined with standard sequential or continuous progesterone or progestin treatment, or with interrupted or pulsed progestin administration, as previously described in, U.S. Pat. Nos. 5,422,119; 5,382,573; 5,256,421 and 5,108,995 and U.S. application Ser. Nos. 09/538,485 and 10/134,455, in those women who have their uterus. The above references are incorporated herein by reference in their entirety.

EXAMPLE 7

Any of the above examples 1 through 6 combined with a continuous dose of progestin equivalent to 2.5 mg of medroxyprogesterone acetate, 100 mg of micronized progesterone or 0.35 to 0.5 mg of norethisterone acetate.

EXAMPLE 8

Any of the above examples 1 through 6 combined with no progestin in the standard estrogen dose phase and combined with 90 μg norgestimate in the ultra-low dose estrogen phase.

EXAMPLE 9

Any of the above examples 1 through 6 combined with no progestin in the standard estrogen dose phase and combined with 90 μg desogestrel in the ultra-low dose estrogen phase.

EXAMPLE 10

Any of the above examples 1 through 6 combined with no progestin in the standard estrogen dose phase and combined with 100 mg micronized progesterone in the ultra-low dose estrogen phase.

EXAMPLE 11

Any of the above examples 1 through 6 combined with no progestin in the standard estrogen dose phase and combined with 0.35 mg norethinedrone in the ultra-low dose estrogen phase.

The following example provides data from a study undertaken to measure the effects of a change in the dose of estrogen in HRT given to two groups of women.

EXAMPLE 12

The study undertaken included two groups of women. The first group of women, identified as group A in Table 1, included 7 women that were postmenopausal and were already being treated with HRT.

The second group of women, identified as Group B in Table 2, included 7 women who were postmenopausal and were not being treated with HRT. As can be seen in Table 2, all of the women in group B had hot flushes prior to the study.

The drugs used in the study were as follows:

The estrogen used was Oestrogel™ manufactured by Laboratories Besins International, France, and was administered transdermally. Oestrogel™ is a 17β estradiol (Estradiol) gel 0.06% (60 mg/100 g)). The conventional dose used was one ruler (around 2 mL) that delivers 2.5 g.

The progesterone used was Utrogestan™ manufactured by Laboratories Besins Iscovesco, France, administered in the form of a tablet containing 100 mg. For this study the dose for the progesterone was 200 mg per day orally for 10 days.

The regimens and doses that were taken during the study were as follows:

For Group A the regimen comprised 3 days of conventional dose, i.e. 2.5 g of Oestrogel™ followed by 3 days of low dose estrogen which was measured using an insulin syringe of 0.01 ml which is equal to about 0.05 g of Oestrogel™. This cycle was repeated continually throughout the study.

Every 50 days the patient would take 10 days of 200 mg of Utrogestan™ orally along with the estrogen, i.e., 50 days of estrogen was followed by 10 days of estrogen and progesterone (days 51-60).

For Group B the regimen comprised 3 days of conventional dose, i.e., 2.5 g, of Oestrogel™ followed by 2 days of low dose estrogen which was measured using an insulin syringe of 0.01 ml which as discussed above was calculated as being equal to about 0.05 g of Oestrogel™.

Every 50 days the patient would take 10 days of 200 mg of Utrogestan™ orally along with the estrogen, i.e., 50 days of estrogen was followed by 10 days of progesterone and estrogen.

The data recorded during the study is provided below in Tables 1 and 2. Table 1 includes data for Group A and Table 2 includes data for Group B. Data on menstrual bleeding was not recorded, although it was observed that some patients had bleeding while some did not. Following the progesterone administration the endometrium was checked in most patients and had an observed thickness of not more than 5 mm.

TABLE 1

Group A patients previously receiving Hormone Replacement Therapy

| Patient Initials | Year of Birth | Age | Symptoms | Complaints | Duration of Treatment | Duration of Previous Treatment |
|---|---|---|---|---|---|---|
| S. Y. | 1950 | 53 | No | No | 8 months | 3 years |
| E. S. | 1949 | 54 | No | No | 6 months | 3 years |
| B. G. | 1947 | 56 | No | No | 1 year | 4 years |
| E. S. | 1950 | 53 | No | No | 9 months | 2 years |
| E. Z. | 1952 | 51 | Slight change - no change treatment | No | 10 months | 2 years |
| S. R. | 1953 | 50 | No | No | 7 months | 3 years |
| S. E. | 1953 | 50 | No | No | 6 months | 1 years |

As can be seen in Table 1, no complaints were observed for the patients in Group A when they were changed from their previous HRT regimen to the new regimen described above. One patient recorded a slight change in symptoms those being occasional hot flushes, however, chose to stay on the new low dose regimen. No changes in vaginal lubrication were recorded for the patients in Group A.

TABLE 2

Group B patients not previously receiving Hormone Replacement Therapy

| Patient Initials | Year of Birth | Age | Symptoms | Time taken for symptoms to disappear | Duration of Treatment | Improvement of Vaginal Lubrication |
|---|---|---|---|---|---|---|
| K. E. | 1957 | 46 | Hot Flushes | 8 days | 4 months | Yes |
| S. M. | 1955 | 48 | Hot Flushes | 10 days | 5 months | No change - good already |
| A. Y. | 1958 | 45 | Hot Flushes | 7 days | 8 months | Yes |
| Y. S. | 1954 | 49 | Hot Flushes | 6 days | 6 months | Yes |
| G. Y. | 1957 | 46 | Hot Flushes | 8 days | 4 months | No change - good already |
| M. K. | 1957 | 46 | Hot Flushes | 7 days | 1 month | Yes |
| K. N. | 1955 | 48 | Hot Flushes | 8 days | 1 month | Yes |

As can be seen in Table 2, the hot flushes that were symptoms for all the patients in Group B disappeared within 6 to 10 days of being placed on the new regimen. Further, improvements were recorded in vaginal lubrication for 5 of the patients in Group B. Improvements in vaginal lubrication may enable the individual to have easier sexual intercourse. The results recorded in this study for both Groups A and B demonstrate the efficacy of the new regimen for reducing or eliminating one or more of the symptoms associated with postmenopausal estrogen deficiency previously recorded, including hot flushes and reduced vaginal lubrication.

While the invention has been described with particular reference to certain embodiments thereof, it will be understood that changes and modifications may be made by those of ordinary skill in the art within the scope and spirit of the following claims.

The invention claimed is:

1. An improved pharmaceutical preparation comprising a plurality of doses arranged in alternating standard dose estrogen phases and ultra-low dose estrogen phases, each phase consisting of from about 1 to about 4 consecutive daily unit doses or an equivalent thereof, wherein the daily unit doses of the standard dose estrogen phases contain an amount of from about 0.5 mg to about 1.0 mg of estradiol, and the daily unit doses of the ultra-low dose of estrogen phases contain an amount selected from-about 0.005 mg to about 0.01 mg of estradiol, for administration to a female in need of estrogen replacement therapy.

2. A pharmaceutical preparation according to claim 1, wherein the daily unit doses are in at least one of orally, transdermally and buccally administerable form.

3. A pharmaceutical preparation according to claim 1, comprising administering a series of consecutive daily doses arranged in standard dose estrogen phases of two daily unit doses each alternating with ultra-low dose estrogen phases of two daily unit doses each.

4. A pharmaceutical preparation according to claim 1, comprising administering a series of consecutive daily doses arranged in standard dose estrogen phases of three daily unit doses each alternating with ultra-low dose estrogen phases of three daily unit doses each.

5. A pharmaceutical preparation according to claim 1, comprising administering a series of consecutive daily doses arranged in standard dose estrogen phases of four daily unit doses each alternating with ultra-low dose estrogen phases of four daily unit doses each.

* * * * *